(12) United States Patent
Lesobre et al.

(10) Patent No.: US 12,011,253 B2
(45) Date of Patent: Jun. 18, 2024

(54) METHOD FOR GENERATING A RESPIRATORY DATUM AND ASSOCIATED DEVICE

(71) Applicant: HAPPLYZ MEDICAL, Pierrefonds (FR)

(72) Inventors: Vanessa Lesobre, Chatou (FR); Maxime Berriot, Chatou (FR)

(73) Assignee: HAPPLYZ MEDICAL, Pierrefonds (FR)

( * ) Notice: Subject to any disclaimer, the term of this patent is extended or adjusted under 35 U.S.C. 154(b) by 0 days.

(21) Appl. No.: 17/924,266

(22) PCT Filed: Jun. 17, 2021

(86) PCT No.: PCT/EP2021/066408
§ 371 (c)(1),
(2) Date: Nov. 9, 2022

(87) PCT Pub. No.: WO2021/255168
PCT Pub. Date: Dec. 23, 2021

(65) Prior Publication Data
US 2023/0181050 A1    Jun. 15, 2023

(30) Foreign Application Priority Data
Jun. 17, 2020 (FR) ..................................... 2006327

(51) Int. Cl.
*A61B 5/08* (2006.01)
*A61B 5/024* (2006.01)
(Continued)

(52) U.S. Cl.
CPC ............ *A61B 5/024* (2013.01); *A61B 5/0803* (2013.01); *A61B 5/087* (2013.01); *A63B 23/18* (2013.01); *A61B 5/14551* (2013.01)

(58) Field of Classification Search
None
See application file for complete search history.

(56) References Cited

U.S. PATENT DOCUMENTS

| | | | |
|---|---|---|---|
| 2015/0027294 A1 | 1/2015 | Johnson | |
| 2019/0134460 A1* | 5/2019 | Cheu ...................... | A63B 23/18 |

(Continued)

FOREIGN PATENT DOCUMENTS

| | | |
|---|---|---|
| CN | 105913721 A | 8/2016 |
| WO | WO 2013/067495 A2 | 5/2013 |

(Continued)

OTHER PUBLICATIONS

International Search Report as issued in International Patent Application No. PCT/EP2021/066408, dated Sep. 17, 2021.

(Continued)

*Primary Examiner* — Meredith Weare
(74) *Attorney, Agent, or Firm* — Pillsbury Winthrop Shaw Pittman LLP

(57) ABSTRACT

A method for generating a respiratory datum for a user includes generating a multimedia instruction that is time-stamped via software of an electronic terminal and transmitting this multimedia instruction to the user via a transmission system; measuring the air pressure in a fluid exhalation chamber of a respiration unit for receiving the air exhaled and/or inhaled by a user; and generating a respiratory datum quantifying the respiratory performance of the user.

19 Claims, 4 Drawing Sheets

(51) Int. Cl.
    *A61B 5/087*     (2006.01)
    *A63B 23/18*     (2006.01)
    *A61B 5/1455*     (2006.01)

(56) References Cited

U.S. PATENT DOCUMENTS

2019/0209044 A1*   7/2019   Hess .................... A61B 5/6898
2022/0022772 A1*   1/2022   Adams ................ A61B 5/7246

FOREIGN PATENT DOCUMENTS

WO     WO 2017/072036 A1     5/2017
WO     WO 2018/011358 A1     1/2018

OTHER PUBLICATIONS

International Preliminary Report on Patentability and the Written Opinion of the International Searching Authority as issued in International Patent Application No. PCT/EP2021/066408, dated Dec. 13, 2022.

* cited by examiner

METHOD FOR GENERATING A RESPIRATORY DATUM AND ASSOCIATED DEVICE

CROSS-REFERENCE TO RELATED APPLICATIONS

This application is the U.S. National Stage of PCT/EP2021/066408, filed Jun. 17, 2021, which in turn claims priority to French patent application number 2006327 filed Jun. 17, 2020. The content of these applications are incorporated herein by reference in their entireties.

FIELD OF THE INVENTION

The invention relates to a method and an associated device for generating a respiratory datum.

PRIOR ART

Exhalation is a voluntary expulsion of air through the loosening of the diaphragm and the contraction of the intercostal muscles. The pressure thus exerted on the lung alveoli releases the air that they contain.

However, certain diseases such as cystic fibrosis, chronic obstructive pulmonary disease and asthma can affect these muscles to the point of causing respiratory failure. It has also been observed that patients cured from Covid19 could be subject to respiratory failure for several months after their recovery.

A training device is known in which the subject inhales into a tube connected to channels in which balls are placed which are going to be lifted by the exhalation of the subject. However, this type of system is monotonous and may become tedious for the patient. Yet, several studies have demonstrated a low observance of patients for chronic diseases such as asthma. Such a system thus presents a risk of the patient not following their treatment correctly, and thus not achieving the optimal results.

The document WO2018/011358 is also known enabling athletes to work and analyze their respiratory capacities by means of a mouthpiece making it possible to measure the exhaled air pressure and to analyze this air pressure. A drawback of this system is that it is not suitable for non-sportsmen who quickly get bored with repetitive exercise and who do not have complete control of their respiration, particularly in terms of the rhythm and responsiveness of the respiratory muscles.

The invention thus aims to provide a method and an associated device allowing users to monitor and improve their respiratory performance.

SUMMARY OF THE INVENTION

According to one aspect, the invention relates to a method for generating a respiratory datum of a user.

Said method comprises:
generating a multimedia instruction that is timestamped via software of an electronic terminal and transmitting this multimedia instruction to the user via a transmission means;
measuring the air pressure in a fluid exhalation chamber of a respiration unit for receiving a volume of air exhaled and/or inhaled by a user;
generating a timestamped respiratory indicator as a function of the measured air pressure,
detecting an interaction on a tactile interface, for example a tactile interface integral with the respiration unit;
generating a timestamped tactile indicator as a function of the detected interaction;
reception by a calculator of the electronic terminal of the respiratory indicator and the tactile indicator;
generating a respiratory datum quantifying a respiratory performance of the user as a function of the correlation of the tactile indicator and the respiratory indicator with the multimedia instruction.

One advantage of the invention is to generate a datum making it possible to measure the respiratory progress of a user. Another advantage is to encourage the user to synchronize his interaction movements with his exhalation and/or his inhalation.

In one embodiment, the respiratory indicator is generated as a function of:
a maximum or average air pressure value measured over a predetermined time interval, and/or
a time during which the air pressure value is above a predetermined threshold.

In one embodiment, the tactile indicator further comprises an identifier of an interaction means on which an interaction has been detected; and/or the duration of the interaction; and/or the intensity of the interaction. One advantage is to discriminate between each tactile interface (or "key" on the unit). In this way, the user can obtain a different effect as a function of the key he presses and/or the multimedia instruction may comprise a tactile interaction instruction on a key. In one embodiment, the device comprises a joystick adapted to be held in one hand of the user and comprising on its surface said tactile interface.

In one embodiment, the timestamped multimedia instruction comprises a respiration instruction and/or an interaction instruction.

One advantage of the presence of tactile instructions is to enable the user to focus less on his respiration, and thus to obtain results that are more representative of the capacities of the user. On the other hand, the tactile instructions allow the user to set a synchronicity that can be used to synchronize his exhalations.

In one embodiment, the respiration instruction comprises a start date and in which the respiratory datum is generated as a function of the start date and timestamping of the respiratory indicator.

In one embodiment, the respiration instruction comprises a value to be reached. In one embodiment, the respiratory indicator comprises a measured maximum or average pressure. In one embodiment, the respiratory datum is generated as a function of said value to be reached and said measured maximum or average pressure.

In one embodiment, the interaction instruction comprises a start date and in which the respiratory datum is generated as a function of said start date and the timestamping of the tactile indicator.

In one embodiment, the interaction instruction comprises a target identifier and the respiratory datum is generated as a function of the target identifier and the identifier of the tactile indicator. One advantage is to be able to integrate in the respiratory datum the reaction time and/or the synchronization capacities of the respiratory muscles of the user. The advantage is to give interaction instructions with a particular key and to detect whether the correct key has indeed been pressed.

In one embodiment, the method further comprises a prior physiological measurement of the user and comprises the issuance of an alert if said physiological measurement is outside of a predefined range of values. One advantage of this embodiment is to prevent the user from carrying out respiratory exercises if this condition does not allow this or presents a risk.

In one embodiment, the physiological measurement comprises a heart rate and/or a blood oxygen saturation rate measured by a reflection oximeter arranged on the surface of the respiration unit. One advantage is to prevent the user from using the device if his blood oxygen level is too low. In fact, respiratory exercises would tend to lower this value, therefore presenting a risk if the user's rate was already too low before the start of the exercise. Another advantage is to monitor a user during an exercise. The user can then continue to train with confidence, because he knows that an alert will be issued in the event where his physiological measurements are too low.

In one embodiment, the method further comprises the determination of a score as a function of the respiratory indicator and the tactile indicator or as a function of the respiratory datum. One advantage is to obtain a reproducible datum making it possible to monitor over the long term the score of the user to see his progress. Another advantage is to be able to compare it with other users.

In one embodiment, the method further comprises displaying an image of an interactive video game on a display, the interactive video game including a controllable element as a function of the respiratory indicator and the tactile indicator or as a function of the respiratory datum. One advantage is to be able to transpose the instructions into a video game allowing the user to be less bored while doing the exercises. One advantage is thus to improve the observance of the user in the treatment of his chronic respiratory disease.

According to another aspect, the invention relates to a device for generating a respiratory datum of a user comprising a respiration unit. The respiration unit comprises an air pressure sensor to measure the air pressure exhaled and/or inhaled by the user and at least two tactile interfaces integral with the respiration unit.

According to an alternative aspect, the invention relates to a device for generating a respiratory datum of a user comprising a respiration unit and at least two tactile interfaces. The respiration unit comprises an air pressure sensor for measuring the air pressure exhaled and/or inhaled by the user. The tactile interfaces may be arranged on a remote joystick.

The device according to one or the other aspect also comprises an electronic terminal comprising a calculator. In one embodiment, the calculator is adapted to execute the steps of the method according to the invention. The device then comprises connection means to connect the respiration unit and/or tactile interfaces to the electronic terminal. One advantage is to allow the user to interact with tactile interfaces arranged on the same object in which he breathes. The user thus only has one object to hold. One advantage is to facilitate exercises comprising simultaneous respiration instructions and tactile interactions. One advantage of remote tactile interfaces of the respiration unit is to be able to reproduce the sensation of a joystick for the user. Another advantage is thus to make it possible to interact more easily without having to raise the arms to hold the respiration unit.

In one embodiment, the device comprises two joysticks that are not integral with one another and each comprising at least one tactile interface such as described above. One advantage is to be able to take one joystick in each hand and thus be able to interact more easily while maintaining full arm mobility.

In one embodiment, the device comprises a communication means connected to the electronic terminal to transmit data to the user. One advantage is that the electronic terminal is mounted in a remote device connected to the respiration unit and/or to the tactile interfaces.

In one embodiment, the device comprises luminous means designed to be lit up as a function of the respiratory indicator and/or the tactile indicator.

In one embodiment, the device comprises a reflective oximeter on the surface of the respiration unit. One advantage is to make it possible to measure the oxygen level in the user's blood before or during the exercises by simply pressing a finger on a portion of the surface of the respiration unit. The user does not need to carry out any specific action to take this type of measurement and does not need to equip himself with a bulky additional device.

In one embodiment, the device comprises a display means. The display means is connected to the electronic terminal and/or to the calculator. One advantage is to enable the display of the multimedia instructions to the user during an exercise. Another advantage is to enable the display of a score or an interactive video game to the user.

In one embodiment, the respiration unit further comprises at least one motion sensor for measuring an inclination angle of said respiration unit. The motion sensor is preferably connected to the electronic terminal. The motion sensor makes it possible to provide angular movement information of the respiration unit. A first advantage is to integrate in the multimedia instruction an angular displacement instruction to distract the attention of the user in order to train his breathing without having the full attention of the user on his breathing.

In one embodiment, the electronic terminal is configured to determine the orientation of the respiration unit from the data provided by the motion sensor. The electronic terminal may comprise the display of a predetermined target orientation of the respiration unit and the generation and the display of an indicator as a function of the orientation of the respiration unit relative to the predetermined target orientation. One advantage is to guide a user on the orientation of the respiration unit. For example, the device may be used for the administration of a therapeutic agent requiring a particular orientation of the respiration unit. In another example, the device may be advantageously used to simulate the administration of a therapeutic agent.

According to another aspect, the invention relates to a computer program product comprising instructions that lead the device according to the invention to execute the steps of the method according to the invention.

According to one aspect, the invention relates to a computer program product comprising instructions which, when the program is executed by a computer, lead the computer to implement the method according to the invention. The computer program product may comprise instructions which, when the program is executed by the calculator of the electronic terminal of the device according to the invention, lead said calculator to implement the method according to the invention.

According to a final aspect, the invention relates to a computer readable support, on which the computer program according to the invention is recorded. Preferably, the device according to the invention comprises such a memory or comprises means of connecting to such a memory.

BRIEF DESCRIPTION OF THE FIGURES

Other characteristics and advantages of the invention will be become clearer on reading the following detailed description, with reference to the appended figures, that illustrate.

DESCRIPTION OF THE INVENTION

In this description, "inhalation" is the respiration phase during which atmospheric air enters the lungs. "Exhalation" is the respiration phase in which air is expelled out of the lungs.

According to a first aspect, the invention relates to a device 100 for generating a respiratory datum. The device 100 for generating a respiratory datum comprises a respiration unit 1. The device 100 may also comprise an electronic terminal 10.

Figure 2A:
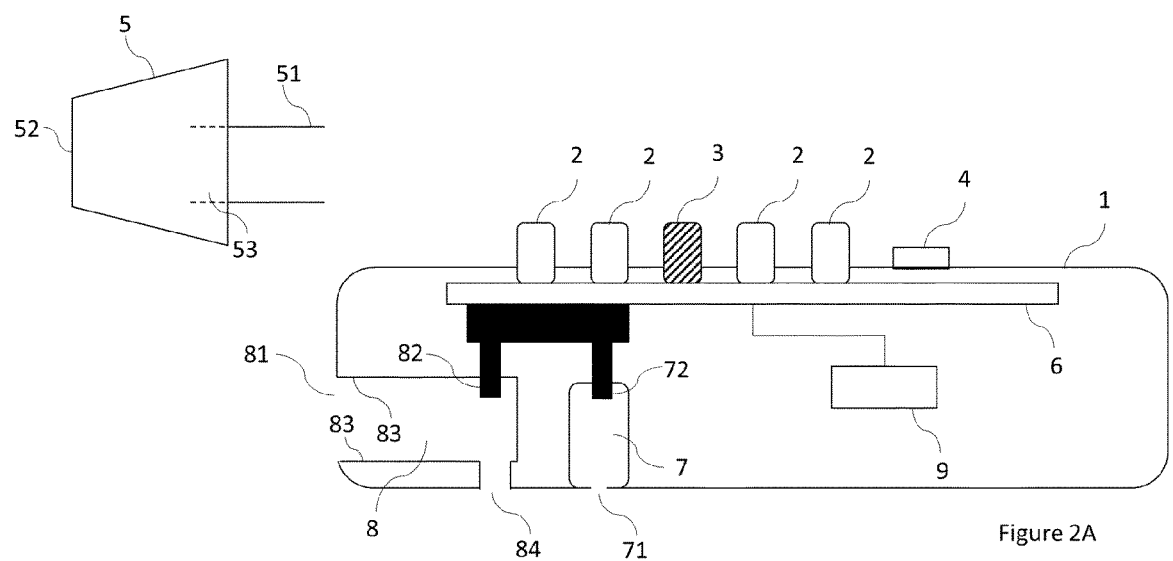
FIG. 2A is a schematic sectional view of a respiration unit and a removable mouthpiece according to one embodiment of the invention comprising an atmospheric chamber and a fluid exhalation chamber connected to an inlet on which a mouthpiece may be mounted. The atmospheric chamber and fluid exhalation chamber each comprise at least one air pressure sensor connected to a printed circuit. The control unit consists of interaction keys connected to the printed circuit.

A first exemplary respiration unit 1 is illustrated in FIG. 2A. The respiration unit 1 comprises a fluid exhalation chamber 8 for receiving the air exhaled by a user.

The respiration unit 1 may comprise a mouthpiece 5 in which the user can place his lips to inhale and exhale.

The mouthpiece 5 comprises an opening 52. The mouthpiece 5 comprises a cavity 53 making it possible to fluidically connect the opening 52 to the main body of the respiration unit, notably to the fluid exhalation chamber 8. In this respect, the mouthpiece comprises a means of connection 51 to an additional means of connection 83 of the respiration unit.

"Fluidic chamber" designates any structure capable of accommodating a volume of fluid for the measurement of pressure in such a structure. A fluidic chamber may in this respect comprise a portion of a fluidic channel.

Preferably, the mouthpiece 5 is attached to the respiration unit in a removable way.

The fluid exhalation chamber 8 comprises a fluidic opening 81. The fluidic opening may be in fluidic communication with the cavity 53 of the mouthpiece 5. The air from the user's inhalation and exhalation then passes through said fluidic chamber, creating respectively a vacuum and overpressure measurable by an air pressure sensor.

One advantage is that it is possible to remove the mouthpiece 5 to be able to clean it without cleaning the entire respiration unit. Another advantage is that the mouthpiece 5 can be replaced to adapt the mouthpiece to the user. The respiration unit is then adapted to be used by different people having a different oral anatomy, notably by changing the size of the removable mouthpiece 5. Another advantage is to be able to adapt the mouthpiece to a particular exercise, for example, an example where the user should exhale with the lips pinched.

In one embodiment not represented, the fluid exhalation chamber 8 comprises a membrane. The membrane is preferably airtight and makes it possible to create a leak tight separation between the pressure sensor 82 and the external environment. The membrane is deformable so as to propagate the air pressure experienced by the membrane to the air present in the fluidic channel 87 between the membrane and the air pressure sensor 82. One advantage is that the fluidic channel and the air pressure sensor are protected from contamination by dust, dirt, bacteria or viruses.

The membrane may be arranged at the fluidic opening 81 or at the fluidic channel 87 or generally between the fluidic opening 81 and the air pressure sensor 82. The membrane may be made of plastic material such as elastomeric material.

When the fluid exhalation chamber 8 comprises a membrane, the air pressure sensor then makes it possible to measure the air pressure exhaled and/or inhaled by the user in the fluid exhalation chamber. Indeed, the portion of the fluidic chamber between the air pressure sensor and the membrane comprises a pressure that varies as a function of the air pressure exhaled and/or inhaled by the user thanks to the deformation of the membrane.

The fluid exhalation chamber 8 is formed by walls 83. At least one of the walls has an air outlet hole 84. The air outlet hole 84 is in fluidic communication with the outside of the respiration unit 1 and allows gasses to escape from the fluidic chamber 8. Preferably, the air outlet hole 84 is arranged transversely or substantially perpendicular to the direction of the gasses in the fluidic chamber through the opening 81. Preferably, the section of the outlet hole 84 is less than the section of the opening 81 of the fluid exhalation chamber 8. This arrangement makes it possible to create a resistance to air exit and to create a pressure in the fluid exhalation chamber 8 that will be able to be measured, preferably during the inhaling and/or exhaling of the user. This air outlet hole 84 may also be designed to allow air in the fluidic channel between the opening of the mouthpiece 52 and the sensor 82 to escape. This then advantageously allows the user to have more time to catch his breath without creating expiratory overpressure in the fluidic channel.

Figure 7:
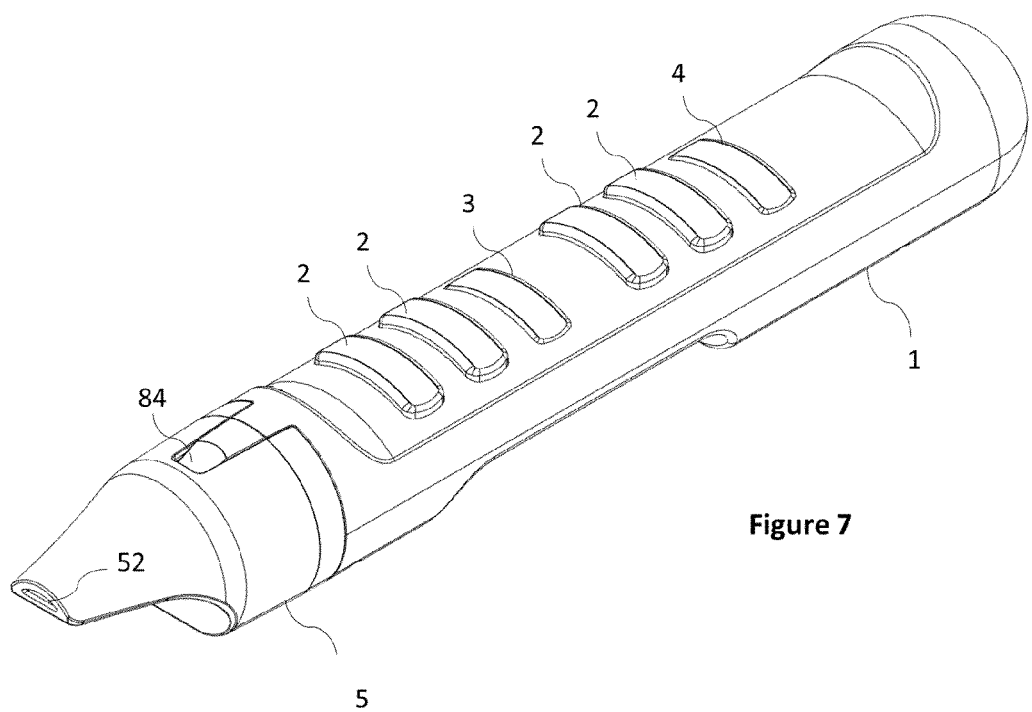
FIG. 7 is a perspective view of one embodiment of a respiration unit on which a mouthpiece is mounted.

In one embodiment, the air outlet hole 84 is arranged on the mouthpiece 5 as illustrated in FIG. 7.

The respiration unit 1 makes it possible to measure the air pressure in the fluid exhalation chamber 8. The respiration unit 1 may, in this respect, comprise an air pressure sensor 82.

The air pressure sensor is preferably constituted of or comprises a pressure-sensitive element to determine an actual pressure applied to the sensor to convert this information into an output signal. The pressure sensor is connected to the electronic terminal so that the output signal is transmitted to the electronic terminal.

The pressure sensor may comprise a pressure-sensitive element on which a pressure gauge is stuck or applied by spray. This pressure sensitive element may comprise a diaphragm.

The air pressure sensor may also comprise a capacitive pressure sensor or a piezoresistive pressure sensor well known to those skilled in the art.

The air pressure sensor 82 may be arranged against a wall 83 of the fluid exhalation chamber 8. The pressure sensor 82 may be arranged in a blind channel 87 in fluidic communication with the fluid exhalation chamber 8.

Figure 2B:
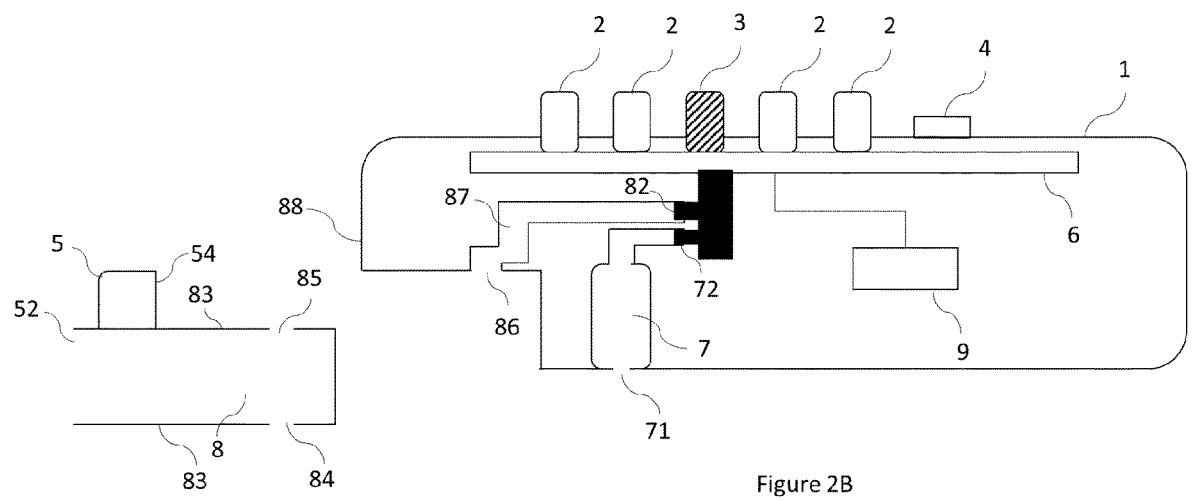
FIG. 2B is a schematic sectional view of a respiration unit and a removable mouthpiece according to one embodiment of the invention in which the fluid exhalation chamber is arranged in the removable mouthpiece.

In a second example illustrated in FIG. 2B, the mouthpiece 5 comprises the fluid exhalation chamber 8. The mouthpiece 5 has an inlet opening 52 through which the user can inhale and exhale. The mouthpiece is removable. The fluid exhalation chamber 8 comprises a second fluidic outlet opening 84 and a third opening 85. Preferably, the second opening 84 and the third opening 85 are arranged on two opposite walls 83 of the fluid exhalation chamber 8.

One advantage of placing the fluid exhalation chamber 8 in the removable mouthpiece 5 is to facilitate cleaning of said chamber and prevent the accumulation of moisture.

In this embodiment, the respiration unit 1 comprises a recess designed to receive the removable mouthpiece 5. In this case, the respiration unit 1 comprises means of cooperation 88 with the removable mouthpiece 5. Preferably, the removable mouthpiece 5 comprises additional means of cooperation 54 for removable attachment to the respiration unit 1.

The respiration unit 1 may comprise a blind (i.e. not opening) fluidic channel 87 extending from an inlet 86. The fluidic channel is in this case a fluidic continuity of the fluid exhalation chamber 8. The fluidic channel comprises an air pressure sensor 82. The air pressure sensor 82 makes it possible to measure the air pressure exhaled by the user. The air pressure sensor 82 makes it possible to measure the air pressure in the fluid exhalation chamber 8. The inlet 86 of the fluidic channel 87 is arranged to cooperate with the third fluidic outlet opening 85 of the fluid exhalation chamber of the mouthpiece when said mouthpiece is mounted on the respiration unit 1.

One advantage of the fluidic channel 87 is that it protects the air pressure sensor 82, notably when handling the respiration unit when the mouthpiece is removed.

The outlet opening 84 allows exhaled air to escape from the fluid exhalation chamber 8 to the outside of the unit 1. The user can then exhale or inhale continuously into the fluid exhalation chamber 8. The interest of this outlet opening 84 is also to create resistance to air entering and exiting the fluidic chamber respectively during inhalation and exhalation. This resistance advantageously makes it possible to increase the pressure caused by inhalation and/or exhalation in the fluid exhalation chamber.

Figure 8:
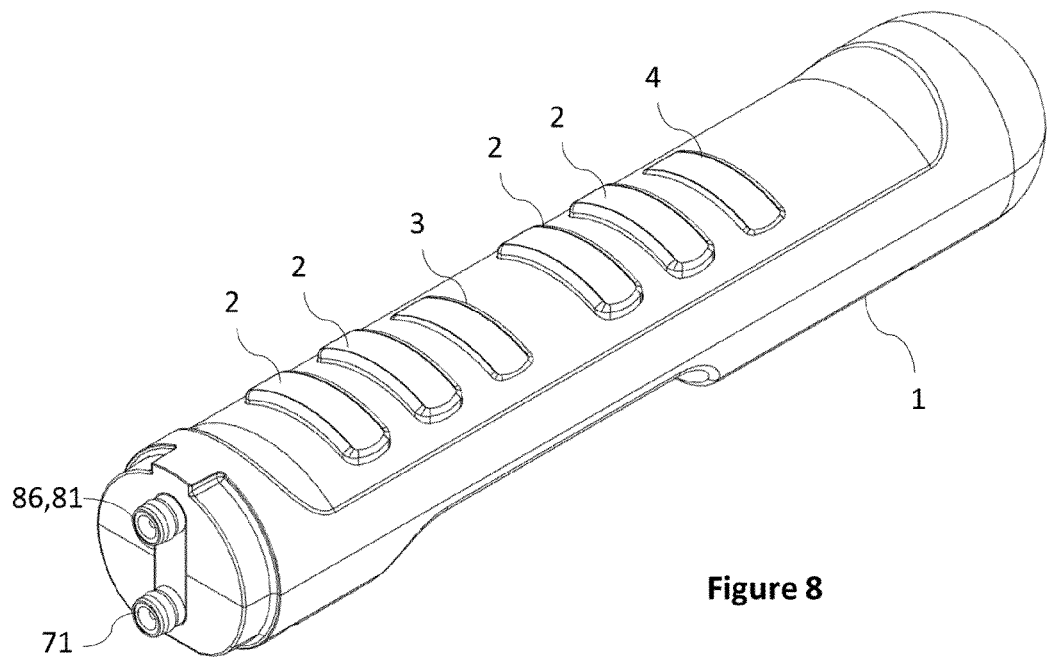
FIG. 8 is a perspective view of a respiration unit according to FIG. 7 without a mouthpiece. The respiration unit comprises two outlets to cooperate with means for connecting the mouthpiece. The outlets are fluidly connected to pressure sensors in the respiration unit. One outlet is intended to be connected to a fluidic outlet of the mouthpiece for receiving the subject's mouth and another outlet is intended to be connected to a fluidic outlet of the mouthpiece to measure the atmospheric pressure when the user inserts the mouthpiece into his mouth.

In one embodiment, the respiration unit 1 comprises an atmospheric fluidic chamber 7. This atmospheric fluidic chamber makes it possible to measure the atmospheric pressure. One advantage is to be able to provide an atmospheric pressure measurement to serve as a baseline for the air pressure measurement in the fluid exhalation chamber 8. The atmospheric fluidic chamber 7 comprises a second air pressure sensor 72 and an outlet hole 71 in fluidic communication with the outside environment, optionally through a channel of the mouthpiece 5. The second air pressure sensor 72 may comprise a differential pressure sensor. The second air pressure sensor 72 is thus advantageously protected. In one embodiment represented in FIG. 8, the outlet hole 71 is arranged to be connected to an open fluidic channel of the mouthpiece. One advantage is that the atmospheric fluidic chamber 7 is enlarged to improve the accuracy of the measured atmospheric pressure.

The mouthpiece 5 may comprise a second opening, a second cavity, a second means of connection, to make a connection with the hole 71 of the atmospheric fluidic chamber 7.

In one embodiment, the atmospheric fluidic chamber 7 also comprises a membrane such as that described for the fluid exhalation chamber 8.

In one embodiment, the mouthpiece 5 comprises a spirometer. The outlet hole 71 may be connected to the user's expiratory pressure in the spirometer. The spirometer may comprise a hollow cylinder through which flows the airflow exhaled or inhaled by the user. In this embodiment, the outlet hole 71 is connected to a first section of said cylinder and the opening 81 of the fluid exhalation chamber is connected to a second section of the cylinder different from the first section. In this way, each air pressure sensor measures a pressure relative to the flow velocity of the air exhaled and/or inhaled at different sections of the cylinder.

The electronic terminal may be configured to generate an indicator illustrating the lung capacity of the individual as a function of the difference in pressures measured by the two air pressure sensors 82, 72.

In one embodiment, the device 100 comprises a plurality of tactile interfaces 2. Preferentially, the tactile interfaces 2 make it possible to detect user interaction. In a first embodiment, the tactile interfaces 2 comprise buttons. A button is illustrated in sectional view in FIG. 3. The button 2 comprises a movable cap 21 on which the user can press with his finger. When pressed, the cap 21 is moved along a predefined path, preferably in a direction that is substantially perpendicular to the surface 26 of the respiration unit 1. Moving the cap 21 may cause a connection piece 24 to move.

The button 2 may comprise a switch whose status is changed as a function of the travel of the connector 24. Preferably, the switch is connected to a printed circuit 6.

Figure 3:
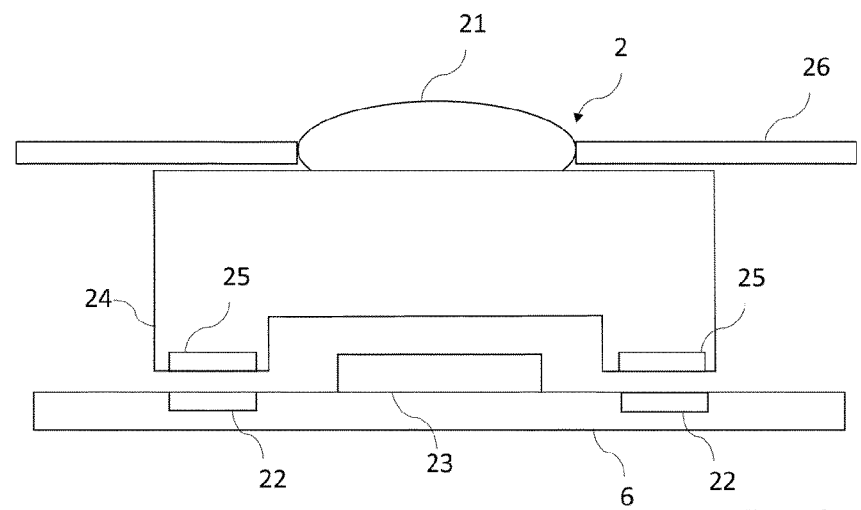
FIG. 3 is a schematic sectional view of an interaction key of a respiration unit.

As illustrated in FIG. 3, the connector 26 may comprise at least one connection track 25. The connection track 25 is arranged to make contact with a connection track 22 of the printed circuit 6 when the connector 26 is at the end of its course. The contact between the two connection tracks 25, 22 is detected and allows an interaction on the user interface to be detected.

In other embodiments, the interfaces may comprise tactile surfaces, holes comprising means for detecting user interaction on said interfaces. The interfaces 2 may also comprise pressure sensors to measure the pressure exerted by the user during an interaction.

In one embodiment, the tactile interfaces 2 are integral with the respiration unit 1. In this case, the tactile interfaces 2 are on the same object as the one in which the user exhales and in which the air pressure is measured. One advantage is to allow the user to exhale and interact with the tactile interfaces simultaneously.

Figure 1:
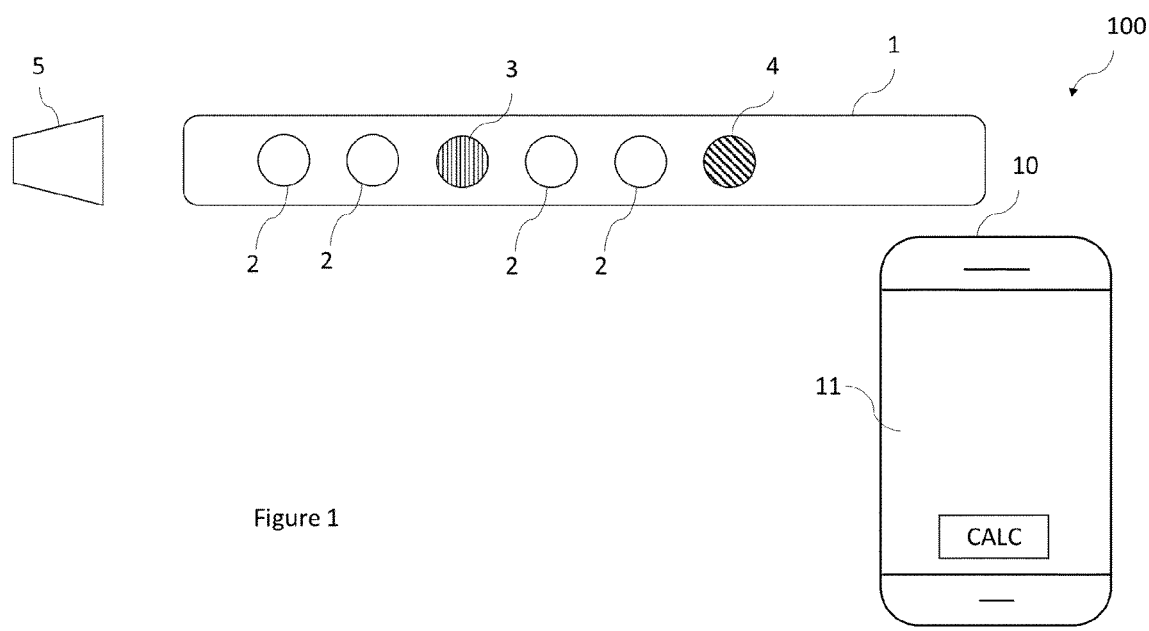
FIG. 1 is a schematic view of a device according to one embodiment of the invention in which the device comprises a mouthpiece mounted on a respiration unit comprising interaction buttons and a probe; the respiration unit being connected to a remote device for data processing and comprising a display for interacting with the user.

In the examples shown in FIGS. 1 and 7, the respiration unit 1 has a flute shape and the tactile interfaces 2 are arranged in the same way as the keys of a flute are arranged. The respiration unit 1 may comprise four tactile interfaces 2. The four tactile interfaces may be aligned with each other and with the opening 52, 81 of the fluid exhalation chamber.

In other embodiments not represented, the respiration unit 1 may have a form of saxophone, or any other type of instrument or wind instrument. In all cases, the tactile interfaces 2 are arranged so that they are accessible to the user's fingers in the same way as a wind instrument.

Preferably, the tactile interfaces 2 are positioned on the surface 26 of the respiration unit 1 so that they are each accessible by a different finger of the user when said user breathes in the mouthpiece 5.

In an alternative embodiment not represented, the tactile interfaces are arranged on the surface of a different object than the respiration unit. For example, the tactile interfaces may be arranged on the surface of a joystick designed to be held by the user's hand. The device may comprise two joysticks, each comprising at least one tactile interface. The tactile interface may be connected to the electronic terminal via a wired or wireless connection such as a Bluetooth, Wi-Fi, or any other wireless connection known to those skilled in the art.

Each tactile interface 2 may be connected to a printed circuit 6. The device 100 is then configured to detect interaction on a tactile interface.

Preferably, the respiration unit 1 may comprise light emission means 23. The light emission means 23 may comprise a light bulb or light emitting diode. The respiration unit may be designed so that the light emission means 23 light up when interaction is detected on an interface. Preferably, each light emission means 23 is associated with an interface and the unit is configured so that each light emission means 23 lights up when an interaction is detected on the associated tactile interface 2. In the embodiment illustrated in FIG. 3, the connector 24 is transparent to light. The connector 24 advantageously allows the light emitted by the light emitting device 23 to pass. In one embodiment, the device is configured to light up the light emission means to transmit information to the user such as low battery level, the status of a connection between the respiration unit 1 and the electronic terminal 10.

In one embodiment, the respiration unit 1 comprises a means of measuring physiological data 3 of the user. Preferably, the physiological data measurement means 3 is a tactile means. The measurement device 3 may be arranged on the surface 26 of the respiration unit. The measuring device 3 is preferably integral with the surface 26 of the respiration unit.

The measuring means preferably comprises a reflective photoplethysmograph or a reflective colorimetric oximeter. A photoplethysmograph or colorimetric oximeter is used to quantify the oxygen saturation of hemoglobin at the level of the blood capillaries and to measure the user's heart rate.

Preferably, the measuring means 3 comprises a light emitter and a sensor of the light reflected by the user, preferably by the user's finger. The emitter and the sensor are therefore positioned on the same surface. One advantage of capturing reflected light rather than transmitted light is that the user does not have to perform any particular action specific to the oxygen saturation measurement. The user simply places his finger on the measuring means 3 to obtain a physiological measurement. The user may advantageously use the device 100 and take measurements during an exercise without having to carry out manipulations that may restrict the exercise and without hampering the freedom of his fingers by a pinch device.

In an example illustrated in FIGS. 1, 2A and 2B, the respiration unit 1 comprises 4 tactile interfaces and comprises a measuring means 3 arranged between 2 tactile interfaces.

In another example not represented, the measuring means 3 may be placed anywhere on the respiration unit 1 that can be accessed by a user's finger when holding the respiration unit. For example, the measuring means may be arranged on the side opposite the side comprising the tactile interfaces 2. One advantage is that the user can rest his thumb on the tactile interface. Thanks to its larger contact area and larger volume, the measurement of physiological data by the user's thumb is advantageously more reliable and/or precise.

In one embodiment, the respiration unit comprises a pad 4. The pad is arranged near tactile interfaces 2. The pad 4 is preferably arranged to rest a user's finger.

One advantage of the pad 4 is that it holds the respiration unit in a balanced manner with at least one finger of the user. Indeed, in the example of a flute-shaped respiration unit, the user's two thumbs are arranged underneath the unit. The middle finger, index and ring finger are placed on top of the respiration unit. The pad 4 advantageously allows the user to maintain the balance of the respiration unit 1, notably without the risk of erroneously interacting with a tactile interface 2.

The pad 4 may comprise a rough or adherent surface such as a surface comprising silicone or spurs. The respiration unit 1 may comprise two or more pads 4, which advantageously makes it possible to rest the fingers that are not used to interface with the tactile interfaces 2 and/or the measuring means 3.

The device 100 according to the invention comprises an electronic terminal 10. The electronic terminal 10 makes it possible to receive and process data from the various sensors of the measuring unit such as air pressure sensor(s) 82, 72, tactile interfaces 2 and/or measuring means 3.

The electronic terminal 10 may be integrated into the measuring unit. In another example illustrated in FIG. 1, the electronic terminal 10 is embedded in a remote device. In this example, the respiration unit 1 comprises a transmitter 9. The transmitter 9 is connected to the various sensors 82, 72, 3, 2 of the respiration unit 1 to receive and transmit measured or detected data to the electronic terminal 10 of the remote device. In an example illustrated in FIGS. 2A and 2B, the respiration unit 1 comprises a printed circuit 6 connected to the different sensors 82, 72, 2, 3 and the printed circuit 6 is connected to the transmitter 9. The printed circuit 6 advantageously enables the retrieval and/or processing of the different measurements and detection for transmission to the transmitter 9 and/or the electronic terminal 10.

The electronic terminal may also be configured to receive information specific to the respiration unit 1. The device may be configured so that the electronic terminal can receive information about the battery status of the respiration unit or about a humidity level in the fluid exhalation chamber 8.

The device 100 may also comprise a means of communication 11. The means of communication 11 makes it possible to transmit information to the user. The means of communication 11 may comprise a sound transmitter or a display. The electronic terminal 10 is connected to said means of communication 11. The means of communication 11 makes it possible to transmit to the user variables measured by the device 100 from the measurements of the air pressure sensor 82 and/or touch interactions detected by the tactile interfaces 2. In one embodiment, the means of communication comprises the light emission means 23 of the respiration unit 1.

The electronic terminal 10 comprises a calculator CALL.

The electronic terminal 10 may comprise a memory, preferably a non-transient memory.

The electronic terminal 10 advantageously enables the received signals to be processed.

Figure 6:
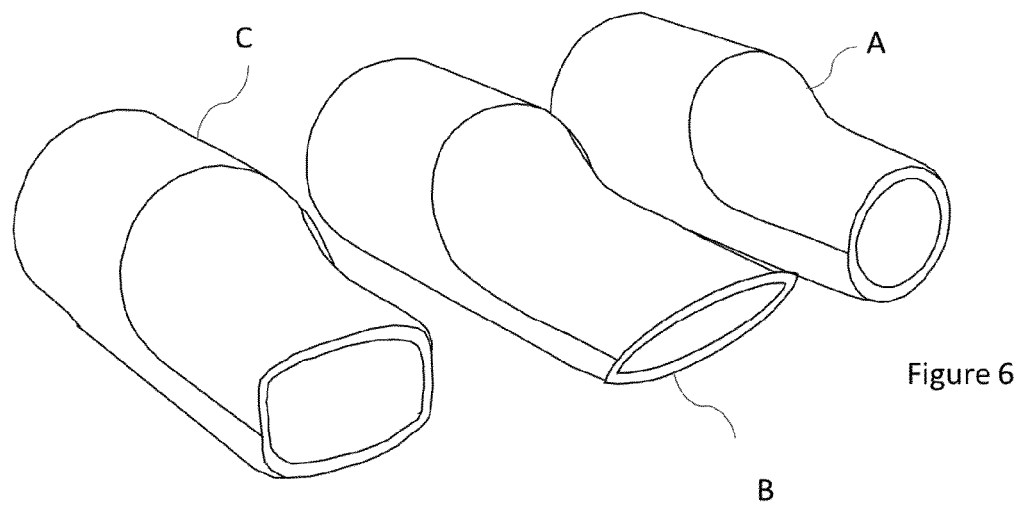
FIG. 6 is a perspective view of three different removable mouthpieces.

According to one embodiment, the device 100 comprises at least two different removable mouthpieces 5. The different mouthpieces notably differ by the surface and the shape of the section of their opening 52. Three types of mouthpiece are described below with reference to FIG. 6.

A first removable mouthpiece A comprises an opening 52 of cylindrical or substantially cylindrical section. The first mouthpiece advantageously makes it possible to maximize the airflow. Indeed, such a section makes it possible to increase the airflow exhaled by the user. One advantage is to make it possible to measure constants by the device, such as lung capacity, maximum expiratory volume per second, peak expiratory flow. Preferably, the section of the opening of the first removable mouthpiece A is comprised between 900 mm$^2$ and 600 mm$^2$ when it is intended for an adult or between 300 mm$^2$ and 420 mm$^2$ when it is intended for a child. The section of the opening of the first removable mouthpiece A may comprise an opening of which the diameter of the section is comprised between 35-25 mm or between 25-20 mm.

In one embodiment, the first removable mouthpiece A comprises a periphery designed to receive by pressing a single-use head of the mouthpiece (not represented). The head of the mouthpiece may comprise a cylindrical portion designed to cooperate with the first removable mouthpiece A. The head of the mouthpiece may comprise any shape that allows it to cooperate with the removable mouthpiece 5.

A second removable mouthpiece B comprises a preferably ovoidal or substantially ovoidal section opening. Preferably, the section of the opening of the second mouthpiece B is between 150 mm$^2$ and 550 mm$^2$ or between 300 mm$^2$ and 400 mm$^2$. The second mouthpiece advantageously allows the user to perform long and deep exhalation exercises.

A third removable mouthpiece C allows the user to perform exercises to promote the excretion of mucous from the user's lungs. The third mouthpiece comprises an oscillating positive expiratory pressure means. The oscillating positive expiratory pressure means causes pulses of resistance when the user exhales. The resistance creates a build-up of positive pressure in the user's lungs which helps keep the respiratory tracts open. In addition, the pulses create vibrations within the respiratory tracts, to help to thin and dislodge mucus that would be too thick or sticky to dislodge by the force of pressure alone. The combined action of pressure and oscillations allows the mucus to move towards the central respiratory tracts, from where it can be pushed out by coughing.

Thus, the device 100 according to one embodiment of the invention comprises at least one mouthpiece or at least two mouthpieces among the first, second and third removable mouthpieces.

Preferably, the device comprises a respiration unit and the three removable mouthpieces: the first, the second and the third. Naturally, other types of removable mouthpieces may be designed and integrated into the device 100, notably for performing specific exercises.

One advantage of these three removable mouthpieces 5 is to be able to obtain, with a single respiration unit 1, three functions of use by replacing only the removable mouthpiece 5. The respiration unit 1 may thus be used for a constant measurement function with the first removable mouthpiece A, for a training function with different types of exhalations (extended exhalation, rapid exhalation) with the second removable mouthpiece B and for an expectoration assistance function (also called inhalotherapy) with the third removable mouthpiece C.

In one embodiment, the device 100 comprises an identifier of the removable mouthpiece 5 that is connected to the respiration unit.

The identifier may comprise electronic means such as a removable mouthpiece connection track detector.

The identifier may comprise magnetic detection means. These magnetic detection means make it possible to detect the mouthpiece connected to the respiration unit when each of the removable mouthpieces comprises a magnetic means, of which the magnetic intensity and/or the position is different from one mouthpiece to another.

The identifier may comprise a means of light detection of a marker of the removable mouthpiece. The identifier may comprise a mechanical detection means. For example, the mouthpiece may comprise a specific mechanical insert designed to cooperate with the respiration unit so that it can be recognized or identified.

A second aspect of the invention relates to a method for generating a respiratory datum S of a user.

Said method preferably comprises the use of a device 100 according to the first aspect of the invention.

The method aims to generate a respiratory datum S quantifying the respiratory performance of the user. The respiratory datum S is generated as a function of the measurements SI made by the air pressure sensor 82 of the fluid exhalation chamber 8.

The method for generating a respiratory datum S aims to transmit a multimedia instruction Cm to the user and measure the user's response to this instruction. The respiratory datum S is next generated from this response. A response of the user may comprise an exhalation measurable by the air pressure sensor 82 of the fluid exhalation chamber 8.

One advantage is to allow transmission to the user of a multimedia instruction Cm and to generate the respiratory datum S as a function of the correlation between the multimedia instruction Cm and the user's response.

In one embodiment of the invention, the response may comprise an interaction SI with one or more of the tactile interfaces 2 of the respiratory unit 1. The user is then prompted to perform exercises in which exhalation and/or finger movement commands are combined. One advantage is that it is possible, for example, to assist the regularity of a respiration rhythm by the beat of a complementary or analogous rhythm with the finger.

Figure 5:
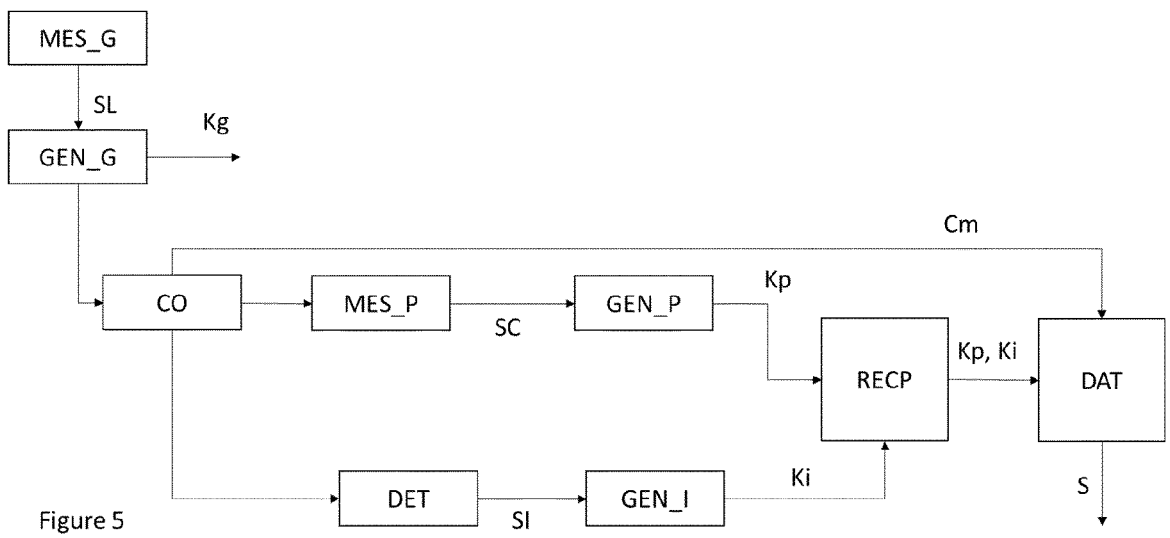
FIG. 5 is a schematic diagram of the method according to one embodiment of the invention.

A method of executing the method according to the invention is described below with reference to FIG. 5.

In one embodiment, the method comprises a physiological measurement MES_G of the user prior to generating the respiratory datum and/or prior to the measurement SC of the air pressure exhaled by the user.

The method may comprise the generation GEN_G and/or issuance of an alert Kg, when the measured physiological value is comprised within a predefined range of values or outside a predefined range of values.

The physiological measurement SL preferably comprises a measurement of the user's heart rate. The physiological measurement SL may also comprise a user's oxygen saturation value of hemoglobin.

One advantage of such a prior measurement is that it allows the user to operate the device safely. Indeed, users suffering from respiratory failure may experience a drop in oxygen in the blood during respiration exercises. This measurement thus makes it possible to detect before the exercise whether the oxygen saturation level in the user's hemoglobin is sufficiently high to enable safe exercise. In this case, a warning message Kg can be issued. The alert message Kg aims to advise the user against starting training with the device. The warning message Kg may comprise a luminous message, for example through the light emission means 23 of the respiration unit. The warning message Kg may comprise an audible message. The warning message Kg may comprise a message displayed on a display. The warning message Kg may comprise a sensory message, for example the vibration of a vibrator arranged in the respiration unit 1. The warning message Kg may cause the respiration unit to stop or block its use.

The physiological measurement SL is preferably measured with the measuring means 3 of the respiration unit 1 described above. One advantage is to allow the user to perform such a measurement by simply placing a finger on the surface 26 of the measuring unit. The user then does not have to move his hands between taking the physiological measurement and using the respiration unit.

In one embodiment of the invention, the method comprises stopping the method or stopping the device, when the measured physiological value SL is within or outside a first predefined value range. In one embodiment, the method comprises generating a respiratory datum S when the measured physiological value is within or outside a second predefined value range.

The method for generating a respiratory datum comprises generating CO a multimedia instruction Cm. The multimedia instruction Cm generated is transmitted to the user. The multimedia instruction Cm may be transmitted to the user via a display 11 or in an audible manner.

The multimedia storage Cm may comprise exhalation instructions.

The generation CO of the multimedia instruction Cm is timestamped or the transmission of the multimedia instruction is timestamped. Timestamping the transmission of the multimedia instruction advantageously allows the transmission dates of the instruction and the user's response to be compared. This comparison makes it possible, for example, to calculate a difference between a target date and the date on which the user performed the action (tactile and/or respiratory) requested by the multimedia instruction.

The multimedia instruction Cm may optionally be generated via software of the electronic terminal 10.

The method for generating a respiratory datum comprises a measurement MEP_P of an air pressure SC exhaled and/or inhaled by a user. The measurement MEP_P of an air pressure may be measured by the air pressure sensor 82 of the exhalation chamber 8 of the respiration unit 1 according to the first aspect of the invention.

The measurements of the air pressure sensor 82 of the fluid exhalation chamber 8 may be recorded on a data storage support, notably in real time.

In one embodiment of the invention, the measurement of an air pressure may comprise the measurement of the air in the fluid exhalation chamber during inhalation and/or during exhalation of the user.

The method for generating a respiratory datum comprises the generation GEN_P of a respiratory indicator Kp.

The respiratory indicator Kp is generated as a function of the measured air pressure SC in the fluid exhalation chamber 8.

The respiratory indicator Kp is timestamped. The method may comprise a step of associating the respiratory indicator with a date. "Date" means a date and a time. The purpose of this timestamping is to record the instant at which the measurement and/or generation of the respiratory indicator was performed.

The respiratory indicator Kp may be generated as a function of the length of an exhalation, as a function of the maximum pressure over a given time period.

In one embodiment, the method also comprises a measurement of the atmospheric air pressure. This measurement is preferably performed by the air pressure sensor 72 of the atmospheric fluidic chamber 7 of the respiration unit 1 according to the first aspect of the invention. The atmospheric air pressure measurement advantageously makes it possible to serve as a standard for the measured air pressure in the fluid exhalation chamber. The measurement of the air pressure SC in the fluid exhalation chamber is then independent of the atmospheric air pressure.

The respiratory indicator Kp may be generated as a function of the measured air pressure SC in the fluid exhalation chamber and as a function of the measured atmospheric air pressure.

The method for generating a respiratory datum may comprise the detection DET of an interaction SI on a tactile interface of the respiration unit 1. An interaction is detected when the user interacts with at least one tactile interface 2 of the respiration unit, for example by contact or by pressing with a finger on at least one tactile interface 2.

A touch indicator Ki is generated GEN_P from or as a function of the detection of an interaction. For example, when the user presses a button on the respiration unit, a signal SI is generated. The generated signal SI is transmitted to a component on the printed circuit and/or electronic terminal. The generated signal makes it possible to detect which interface has undergone an interaction.

The tactile indicator Ki may comprise an identifier of the interface on which an interaction was detected, for example an identifier of the button on which a pressure of the user was detected. The tactile indicator Ki comprises a timestamping of the detection of the interaction. The indicator may comprise an intensity of the interaction, for example, the amount of time the user presses a tactile interface 2 or the force with which the user presses on the tactile interface 2.

The tactile indicator Ki and/or the respiratory indicator Kp are transmitted to a calculator CALC of the electronic terminal 10. As previously described, the electronic terminal 10 may be placed in the respiration unit 1 or in a remote device.

From these two timestamped indicators and from the timestamped multimedia instruction Cm, a respiratory datum S is generated. The respiratory datum S is preferably generated by the calculator CALC.

The respiratory datum S is generated as a function of the correlation of the two indicators Ki, Kp with the multimedia instruction Cm. The respiratory datum S makes it possible to quantify a respiratory performance of the user. For example, the respiratory datum S may comprise a score of 34, the value of which increases when the tactile indicator Ki and the respiratory indicator Kp comply with the multimedia instruction Cm.

In a first example, the multimedia instruction Cm may comprise respiration instructions and synchronized tactile interaction instructions. The respiration instructions comprise successive exhalation instructions at least on one given date, and preferably in a synchronized manner, for example at a given tempo. The interaction instructions comprise an instruction for interaction with the tactile interfaces on at least one given date, preferably in a synchronized manner. The respiration instructions may also comprise dated inhalation instructions. The instructions may be transmitted to the user and comprise one or more target exhalation dates and one or more target tactile interaction dates and/or several target inhalation dates. The instructions may also comprise at least one tactile interface identifier associated with each tactile interaction target date. Preferably, the target dates are synchronized, so as to follow a tempo or a piece of music.

The respiratory Kp and tactile Ki indicators generated are then compared with the multimedia instruction Cm. Notably, the timestamping of the respiratory Kp and tactile Ki indicators are compared with the target dates comprised in the multimedia instruction Cm. The respiratory datum S may be generated as a function of the differences between the timestamps of the indicators and the target dates of the multimedia instruction. In one embodiment, the identifiers of the tactile target dates are compared with the identifiers of the generated tactile indicators Ki and the respiratory datum is generated as a function of this comparison.

On the one hand, the presence of tactile instructions allows the user to focus less on his respiration, and thus obtain results that are more representative of the user's capacities. On the other hand, the tactile instructions allow the user to set a synchronicity that can be used to synchronize his exhalations.

Figure 4:
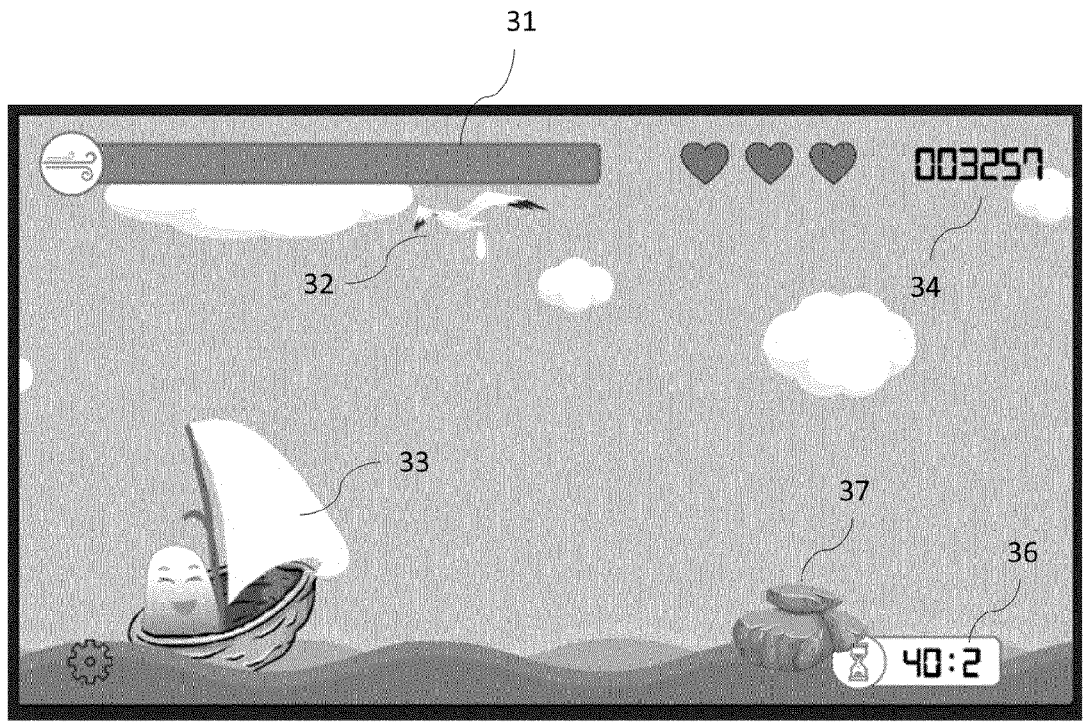
FIG. 4 is a view of the display of a video game according to one embodiment of the invention.

In a second example, the multimedia instruction Cm may consist in moving a controllable element of an interactive video game displayed on the display 11. The controllable element 33 is controllable by the exhalation of the user and/or by interactions on tactile interfaces. In one example shown in FIG. 4, the transmission of the multimedia instruction Cm comprises displaying a controllable element 33 of an interactive video game (here a boat). The boat can be controlled by the user's exhalation to advance the boat linearly and by tactile interaction to jump the boat or vice versa. An exhalation bar 31 allows the user to view the variation in the respiratory indicator Kp. The respiratory indicator Kp makes it possible to advance the controllable element 33. The multimedia instruction Cm may also comprise the display of obstacles such as seagull droppings 32 and rocks 37. The multimedia instruction Cm may then comprise an instruction to avoid said obstacles 32, 37 by moving forward and jumping. The multimedia instruction Cm may comprise an instruction to interact with at least one tactile interface when the controllable element 33 is near or in contact with an obstacle, for example to pick up objects.

The respiratory datum S is then generated as a function of the number of obstacles avoided and as a function of the time to complete a route and/or according to the distance traveled by the controllable element 33 in the interactive game in a given time. A score 34 and a timer 36 may be displayed.

In a third example, the multimedia instruction Cm comprises the display of a route comprising a start and a finish and a controllable element to move from the start to the finish. The movement of the controllable element is activated by the respiratory indicator and the direction of movement may be controlled by the tactile indicator or vice versa. The respiratory datum is then a function of the time taken to complete the route and/or on the number of obstacles avoided.

In another example, the multimedia instruction Cm comprises a respiration instruction comprising a target exhalation time and/or a target exhalation force to be reached by the user. The respiration instruction may comprise a number of target exhalations to be reached within a predefined time. The interaction instructions may comprise a target interaction simultaneously with a target exhalation. The respiration datum S may then be generated as a function of the respiratory indicator Kp. The respiratory datum S may be generated so as to correspond to a respiratory constant such as lung capacity, maximum expiratory volume per second or peak expiratory flow.

In one embodiment, the device 100 comprises means of connection to a network. The device 100 may be designed to compare the breathing datum S generated with respiratory data of other users in real time or using historical usage data. In one embodiment, a device may then generate multimedia instructions and transmit them via the network to each user's device. Thus, each user can receive the same multimedia instructions, allowing "multi-player" type use.

In one embodiment, the device 100 comprises a plurality of respiration units 1 and an electronic terminal 10. The electronic terminal is designed to be connected to at least two respiration units 1 simultaneously to generate simultaneously a respiration datum S for each respiration unit 1 simultaneously. One advantage is that the device may be used in multiplayer mode with a friend or caregiver.

In one embodiment of the invention, the method comprises a prior step of detecting the removable mouthpiece 5. Thus, the type of removable mouthpiece 5 connected to the respiration unit 1 is determined. The multimedia instruction Cm may be generated as a function of the type of removable mouthpiece 5 connected to the respiration unit 1 that has been detected. In an alternative embodiment, a device interface allows the user to select the type of removable mouthpiece A, B, C.

The respiratory datum S may be stored in a memory of the electronic terminal, transmitted to a network and/or transmitted to a third party device. One advantage is thus to be able to monitor the user's progress as a function of the rehabilitation or treatment period. Another advantage is that the data is transmitted or made accessible to a relative of the user and/or to caregivers involved in the user's respiratory follow-up. The respiratory data may comprise user respiratory constants. The breathing data S may be presented in the form of a history, a graph or a rolling table. The transmission to a network or a third party may be carried out by the user's activation, for example by sending an e-mail or a direct transfer from the electronic terminal 10. The respiratory data may be encrypted or protected by a security key or a password.

Preferably, the electronic terminal 10 of the device 100 comprises a calculator CALC adapted or designed to execute the steps of the method for generating a respiratory datum according to the invention.

According to another aspect, the invention relates to a computer program product comprising instructions that lead the device 100 according to the invention to execute the steps of the method according to the invention.

The electronic terminal 10 may comprise a support that can be read by the calculator CALL or by a computer, on which said computer program is stored. Said support may comprise a non-transient memory.

According to another aspect, the invention relates to such a medium on which said computer program is recorded.

By using tactile interfaces in addition to respiration, the device and the method according to the invention thus allow a greater variety of interactive exercises, make it possible to distract the attention of the user from his respiration and help the user to reach a target exhalation rhythm by playing the same rhythm or a rhythm associated with one or more fingers at the same time. Associated rhythm means a rhythm sharing the same tempo with the exhalation rhythm.

The device thus enables the user to work on exhalation, both in terms of lung capacity (exhaled air volume, exhalation power) and in terms of muscle reactivity (reaction speed, ability to maintain a rhythm) as a function of the different multimedia instructions.

According to another aspect, the respiration unit comprises means making it possible to determine the orientation of said respiration unit.

The respiration unit may comprise in this respect a motion sensor. The motion sensor may consist of one or more accelerometers to calculate the linear acceleration along 1 axis. Preferably, the motion sensor comprises 3 accelerometers to calculate a linear acceleration along 3 orthogonal axes. In one embodiment, the motion sensor comprises one or more gyrometers to calculate a rotation or angular velocity according to an angle such as the roll, pitch or heading angle). Preferably, the motion sensor comprises 3 gyrometers to calculate a rotation or an angular velocity along 3 orthogonal axes.

In one embodiment, the motion sensor comprises an inertia unit. The inertia unit preferably comprises 3 accelerometers to calculate a linear acceleration along 3 orthogonal axes and 3 gyrometers to calculate an angular acceleration along 3 orthogonal axes. The motion sensor is preferably integrated in the respiration unit of the device.

The motion sensor is connected to the electronic terminal so as to communicate the measured data to the electronic terminal.

The device is designed to generate the orientation of the respiration unit. The device is preferably configured to generate and display an orientation indicator. The orientation indicator may be calculated as a function of the orientation of the respiration unit and/or a predetermined target orientation. The display of such an indicator may be displayed on a display or may be generated by the LEDs of the device. Orientation means is preferably taken to designate the inclination angle of the respiration unit in relation to a horizontal plane of the Earth's baseline.

The advantage of such a mode is described below.

The respiration unit may be used within the context of support for taking a therapeutic agent for respiratory diseases. This agent may include a drug powder, a drug gas or a drug nebulized solution. The agent must be inhaled by the user according to a specific orientation.

In one embodiment, the device is configured to send the user a message when the orientation of the respiration unit is within a predetermined target angle range.

In certain cases, the agent must be inhaled by the user according to a specific orientation. In one embodiment, the device is configured to transmit a message to the user when the inhalation force measured by the respiration unit is within a predetermined target range.

The message may comprise an audible alert and/or a color change of a LED and/or the generation of a vibration of the respiration unit and/or a message displayed on a display.

The user is then advantageously assisted in performing inhalation of the drug agent with the appropriate orientation and/or inhalation force.

In one embodiment, the mouthpiece may comprise a receptacle for receiving or storing such a therapeutic agent so as to be inhaled by the user breathing in through the opening of the mouthpiece.

In another example, the respiration unit is used to reproduce the taking of such a therapeutic agent. In this case, the respiration unit provides the user with a means of training to simulate the taking of such a therapeutic agent, in particular to provide training on the orientation of the device and the inhalation force to be exerted to properly take the therapeutic agent.

The invention claimed is:

1. A device for generating a respiratory datum for a user comprising:
    a respiration unit comprising:
        an air pressure sensor for measuring the air pressure exhaled and/or inhaled by the user in a fluid exhalation chamber;
    at least two tactile interfaces; and
    an electronic terminal comprising a calculator adapted to execute:
        generating a multimedia instruction that is timestamped,
        transmitting the multimedia instruction to the user via a communication means, said multimedia instruction comprising a respiration instruction and a tactile interaction instruction, and
        in response to transmitting said multimedia instruction to the user:
            receiving a measurement of an air pressure measured by the air pressure sensor;
            generating a timestamped respiratory indicator as a function of the measured air pressure;
            detecting an interaction on at least one of the tactile interfaces;
            generating a timestamped tactile indicator as a function of the interaction detected; and
            generating a respiratory datum quantifying the user's respiratory performance calculated based on a first comparison between the timestamped tactile indicator and the tactile interaction instruction, and a second comparison between the timestamped respiratory indicator and the respiration instruction.

2. The device according to claim 1, further comprising a reflection oximeter connected to the electronic terminal.

3. The device according to claim 1, wherein the communication means comprises a display for displaying the multimedia instruction.

4. The device according to claim 1, wherein the interaction instruction comprises a start date and wherein the respiratory datum is generated as a function of said start date and the timestamping of the tactile indicator.

5. The device according to claim 1, wherein the respiratory unit further comprises a means of measuring a physiological value of the user, and wherein the calculator is adapted to generate an alert if said measured physiological value is outside a predefined range of values.

6. The device according to claim 5, wherein the physiological measurement comprises a heart rate and/or blood oxygen saturation rate measured by a reflection oximeter arranged on the surface of the respiration unit.

7. The device according to claim 1, wherein the respiration unit further comprises at least one motion sensor to measure an inclination angle of said respiration unit.

8. The device according to claim 1, wherein the communication means comprises a display that is adapted to display an image of an interactive video game on an interactive video game including a controllable element as a function of the respiratory indicator and the tactile indicator or as a function of the respiratory datum.

9. The device according to claim 1 wherein the respiration instruction comprises a dated inhalation instruction and/or an exhalation instruction.

10. The device according to claim 1, wherein the tactile interaction instruction comprises an instruction for interaction with at least one of the at least two tactile interfaces on at least one given date.

11. The device according to claim 1, wherein the tactile interaction instruction comprises one or more target tactile interaction dates and the first comparison comprises a comparison between said one or more target tactile interaction dates and a date of the timestamped tactile indicator.

12. The device according to claim 11, wherein the respiratory datum is generated as a function of differences between the timestamps of the indicators and the target dates of the multimedia instruction.

13. The device according to claim 1, wherein the respiration instruction comprises one or more target inhalation or exhalation dates and the second comparison comprises a comparison between said one or more target inhalation or exhalation dates and a date of the timestamped respiratory indicator.

14. The device according to claim 1, wherein the respiration instruction comprises a target exhalation time and/or a target exhalation force to be reached by the user.

15. A non-transitory computer program product comprising instructions that cause the device according to claim 1 to implement a method, the method comprising:
   generating the multimedia instruction that is timestamped via software of the electronic terminal,
   transmitting the multimedia instruction to the user via the communication means, said multimedia instruction comprising a respiration instruction and a tactile interaction instruction, and
   in response to transmitting said multimedia instruction to the user:
      measuring the air pressure exhaled and/or inhaled by the user in the fluid exhalation chamber of the respiration unit;
      generating the timestamped respiratory indicator as a function of the measured air pressure,
      detecting the interaction on at least one of the tactile interfaces;
      generating the timestamped tactile indicator as a function of the interaction detected; and
      generating the respiratory datum quantifying the user's respiratory performance calculated based on the first comparison between the timestamped tactile indicator and the tactile interaction instruction, and the second comparison between the timestamped respiratory indicator and the respiration instruction.

16. The non-transitory computer program product according to claim 15, wherein the interaction instruction comprises a start date and wherein the respiratory datum is generated according to said start date and timestamping of the tactile indicator.

17. The non-transitory computer program product according to claim 15, wherein the instructions comprise an instruction for measuring a physiological value of the user and an instruction for generating an alert if the measured physiological value is outside a predefined range of physiological values.

18. The non-transitory computer program product according to claim 17, wherein the physiological measurement comprises a heart rate and/or blood oxygen saturation rate measured by a reflection oximeter arranged on the surface of the respiration unit.

19. The non-transitory computer program product according to claim 15, wherein the instructions comprise an instruction for displaying an image of an interactive video game on a display, the interactive video game including a controllable element as a function of the respiratory indicator and the tactile indicator or as a function of the respiratory datum.

* * * * *